(12) United States Patent
Otawara

(10) Patent No.: US 7,914,441 B2
(45) Date of Patent: Mar. 29, 2011

(54) ENDOSCOPE

(75) Inventor: Takashi Otawara, Tokyo (JP)

(73) Assignee: Olympus Corporation (JP)

( * ) Notice: Subject to any disclaimer, the term of this patent is extended or adjusted under 35 U.S.C. 154(b) by 706 days.

(21) Appl. No.: 11/647,093

(22) Filed: Dec. 28, 2006

(65) Prior Publication Data

US 2007/0249898 A1    Oct. 25, 2007

Related U.S. Application Data

(63) Continuation of application No. PCT/JP2005/012226, filed on Jul. 1, 2005.

(30) Foreign Application Priority Data

Jul. 2, 2004   (JP) .................................. 2004-197308

(51) Int. Cl.
    *A61B 1/00*   (2006.01)
(52) U.S. Cl. ........ 600/107; 600/104; 600/106; 600/127; 600/129
(58) Field of Classification Search .......... 600/106–107, 600/118, 129, 131
    See application file for complete search history.

(56) References Cited

U.S. PATENT DOCUMENTS

| | | | | |
|---|---|---|---|---|
| 3,897,775 A | * | 8/1975 | Furihata ........................ | 600/131 |
| 3,915,157 A | * | 10/1975 | Mitsui ........................... | 600/107 |
| 4,407,273 A | * | 10/1983 | Ouchi ............................ | 600/107 |
| 4,841,949 A | * | 6/1989 | Shimizu et al. ................ | 600/107 |
| 5,323,768 A | * | 6/1994 | Saito et al. ..................... | 600/106 |
| 5,343,853 A | * | 9/1994 | Komi ............................. | 600/107 |
| 5,868,663 A | * | 2/1999 | Katsurada et al. ............. | 600/107 |
| 6,458,074 B1 | * | 10/2002 | Matsui et al. .................. | 600/106 |
| 6,582,357 B2 | * | 6/2003 | Ouchi et al. ................... | 600/107 |
| 6,605,033 B1 | * | 8/2003 | Matsuno ........................ | 600/107 |
| 6,824,509 B2 | * | 11/2004 | Yamaya et al. ................ | 600/106 |
| 7,087,010 B2 | * | 8/2006 | Ootawara et al. .............. | 600/104 |
| 2002/0091303 A1 | | 7/2002 | Ootawara et al. .............. | 600/106 |
| 2003/0040657 A1 | * | 2/2003 | Yamaya et al. ................ | 600/107 |

FOREIGN PATENT DOCUMENTS

| | | |
|---|---|---|
| JP | 06-315461 | 11/1994 |
| JP | 2001-029312 | 2/2001 |
| JP | 2002-34905 | 5/2002 |
| JP | 2003-116777 | 4/2003 |
| JP | 2004-236715 | 8/2004 |
| WO | WO 01/78581 A1 | 10/2001 |

OTHER PUBLICATIONS

International Search Report dated Aug. 23, 2005.

* cited by examiner

*Primary Examiner* — Matthew J Kasztejna
(74) *Attorney, Agent, or Firm* — Ostrolenk Faber LLP

(57) ABSTRACT

An endoscope includes an insertion portion and a treatment instrument insertion channel, and is inserted into a body cavity; an operation portion which is connected to a proximal end side of the insertion portion; and a treatment instrument raiser which has a guiding surface for guiding a treatment instrument, and able to rise according to an operation from the operation portion. The raiser includes a slit which is formed on a distal end side of the guiding surface and with which a guide wire guided toward the distal end side opening can be engaged, and a guide wire guiding unit which is formed on an outer periphery of the guiding surface and serves to guide the guide wire into the slit. The guide wire is guided into the slit by the guiding unit, when the raiser is raised by the operation from the operation portion.

5 Claims, 12 Drawing Sheets

ENDOSCOPE

CROSS-REFERENCE TO RELATED APPLICATIONS

This application is a continuation of PCT international application Ser. No. PCT/JP2005/012226 filed Jul. 1, 2005 which designates the United States, incorporated herein by reference, and which claims the benefit of priority from Japanese Patent Application No. 2004-197308, filed Jul. 2, 2004, incorporated herein by reference.

BACKGROUND OF THE INVENTION

1. Field of the Invention

The present invention relates to an endoscope and an endoscopic system to which the endoscope is applied, and more particularly to an endoscope which includes an insertion portion having a distal end side opening of a treatment instrument insertion channel in a distal end portion, and which is employed for a desirable treatment with a use of a guide wire made to stick out from the distal end side opening and guided to an affected area, and an endoscopic system to which the endoscope is applied.

2. Description of the Related Art

In recent years, so called side-looking type endoscopes provided with an imaging optical system at a distal end portion of an insertion portion are employed for treatments of affected areas in alimentary tract system, pancreaticobiliary duct system, and the like. The side-looking type endoscope is employed for treatments such as a preparatory treatment, in which contrast agent is injected into a bile duct or a pancreatic duct before diagnosis, and a therapeutic treatment, in which a gallstone present in a common bile duct or the like is removed with a use of a balloon, a grasper, or the like.

When the treatment is performed on the pancreatic duct, bile duct, hepatic duct, or the like with the use of the endoscope, the distal end portion of the insertion portion of the endoscope is inserted into a duct to be treated such as the pancreatic duct, bile duct, hepatic duct, or the like. However, since the pancreatic duct, bile duct, hepatic duct, and the like are extremely thin ducts, the insertion of the distal end portion of the insertion portion of the endoscope is not easy. Therefore, a following procedure is generally taken.

First, the distal end portion of the insertion portion of the side-looking type endoscope is inserted into an area around a duodenal papilla. Then, while keeping the area under radioscopy, the operator guides the guide wire penetrating through the treatment instrument insertion channel and makes the guide wire stick out from an opening which opens in a lateral direction in the distal end portion of the insertion portion of the endoscope, and further inserts the guide wire into a desired duct to be treated such as the pancreatic duct, bile duct, hepatic duct, or the like. Thereafter, the operator inserts a treatment instrument such as a catheter into the desirable duct to be treated such as the pancreatic duct, bile duct, hepatic duct, or the like using the guide wire as a guide.

Here, the guide wire or the treatment instrument runs in an axial direction of the insertion portion of the endoscope. Therefore, the guide wire and the treatment instrument advance in the same direction. When one desires to insert the guide wire or the treatment instrument through the opening of the treatment instrument insertion channel in the distal end portion of the insertion portion and into a duct such as the pancreatic duct, bile duct, hepatic duct, or the like, he/she needs to change the direction of advance of the guide wire or the treatment instrument around the opening of the insertion portion. For this purpose, the side-looking type endoscope has a treatment instrument raiser in the distal end portion of the insertion portion. The operator can change the direction of advance of the guide wire or the treatment instrument which advances in the axial direction of the insertion portion to a radial direction by raising the treatment instrument raiser.

Thus, once the guide wire is inserted into the extremely thin duct such as the pancreatic duct, bile duct, hepatic duct, or the like, the operator can insert and withdraw various types of treatment instruments into and out of the duct using the guide wire as a guide.

When the treatment instrument is withdrawn from the pancreatic duct, bile duct, or hepatic duct, the guide wire is sometimes withdrawn together with the treatment instrument against the will of the operator due to close contact between the treatment instrument and the guide wire. Since the pancreatic duct, bile duct, or hepatic duct is an extremely thin duct, as described above, the insertion of the guide wire thereinto is difficult to perform. Therefore, it is extremely cumbersome and troublesome for the operator to reinsert the guide wire into the pancreatic duct, bile duct, hepatic duct or the like.

Hence, the operator needs to devise some ways to prevent the withdrawal of the guide wire on removing the treatment instrument from the pancreatic duct, bile duct, hepatic duct, or the like. For the above purpose, conventionally, after the operator moves the treatment instrument to a certain extent in a direction of withdrawal, an assistant of the operator pushes back the guide wire, which moves together with the treatment instrument, towards a direction of the pancreatic duct, bile duct, hepatic duct, or the like. Alternatively, the guide wire is held so as not to move and be withdrawn together with the treatment instrument, for example. Such an operation is extremely cumbersome and requires plural personnel, i.e., at least the operator and the assistant. As can be seen from the foregoing, the endoscopic diagnosis and treatment take long time for treatment due to the cumbersome operation, and places higher financial burden on both the hospital and the patient since its operation needs many personnel.

To solve the problems as described above, some propose an endoscope having a mechanism including a treatment instrument raiser which can secure the guide wire at a predetermined position when raised up. For example, see Japanese Patent Application Laid-Open No. 2002-34905 and Japanese Patent Application Laid-Open No. 2003-116777.

The endoscope described in Japanese Patent Application Laid-Open No. 2002-34905 has a slit for securing the guide wire on a top of a guiding surface of the treatment instrument raiser. When the treatment instrument raiser is raised, the guide wire is engaged with the slit of the treatment instrument raiser, thereby secured relative to the endoscope.

On the other hand, the endoscope described in Japanese Patent Application Laid-Open No. 2003-116777 has a guide wire engaging groove to secure the guide wire on a guiding surface of the treatment instrument raiser, and a guide wire securing mechanism near a forceps channel opening in an operation portion.

The endoscopes according to the documents mentioned above, secure the guide wire relative to the endoscope between the treatment instrument raiser and a predetermined portion of the distal end portion of the insertion portion of the endoscope while the treatment instrument is withdrawn. Thus, these endoscopes can prevent the withdrawal of the guide wire from the pancreatic duct, bile duct, hepatic duct, or the like at the time of removal of the treatment instrument.

However, the guide wire, which has an elongated shape though hard, is not always parallel with the axial direction of the endoscope at a position right out from the treatment instrument insertion channel. Therefore, the axial direction of the guide wire can take any direction on the guiding surface of the treatment instrument raiser.

SUMMARY OF THE INVENTION

An endoscope according to an aspect of the present invention includes an insertion portion which has a distal end hard portion at a distal end side and a treatment instrument insertion channel inside, and is inserted into a body cavity; an operation portion which is connected to a proximal end side of the insertion portion; and a treatment instrument raiser which is arranged near a distal end side opening of the treatment instrument insertion channel in the insertion portion, has a treatment instrument guiding surface for guiding a treatment instrument, and able to rise according to an operation from the operation portion. The treatment instrument raiser includes a slit which is formed on a distal end side of the treatment instrument guiding surface and with which a guide wire guided toward the distal end side opening of the treatment instrument insertion channel can be engaged, and a guide wire guiding unit which is formed on an outer periphery of the treatment instrument guiding surface and serves to guide the guide wire into the slit. The guide wire is configured to be guided into the slit by the guide wire guiding unit, when the treatment instrument raiser is raised by the operation from the operation portion.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of the present invention will be described below with reference to the drawings. It should be noted that the present invention is not limited to the embodiments.

Figure 1:
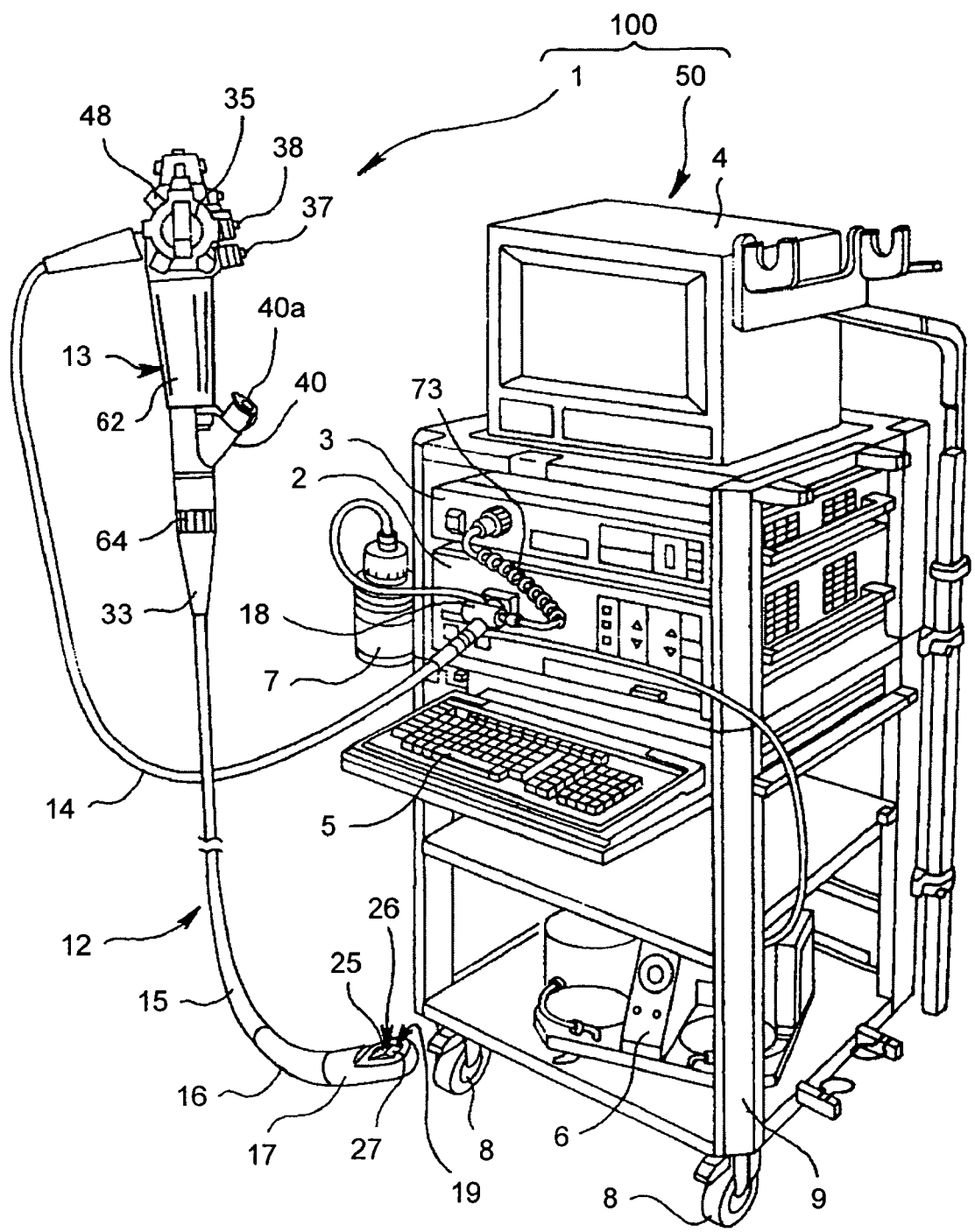
FIG. 1 is a perspective view showing a schematic structure of an endoscopic system including an endoscope according to an embodiment of the present invention.
Figure 2:
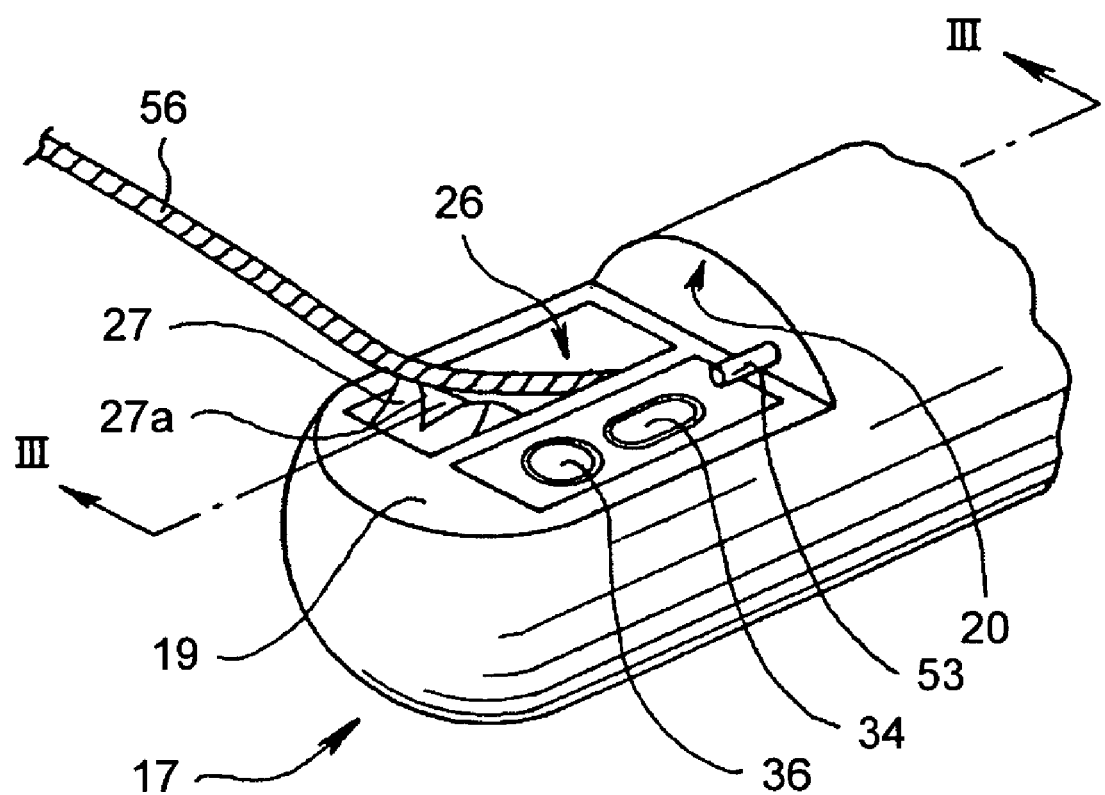
FIG. 2 is an enlarged perspective view of a relevant portion of a distal end portion of the endoscope of FIG. 1.
Figure 3:
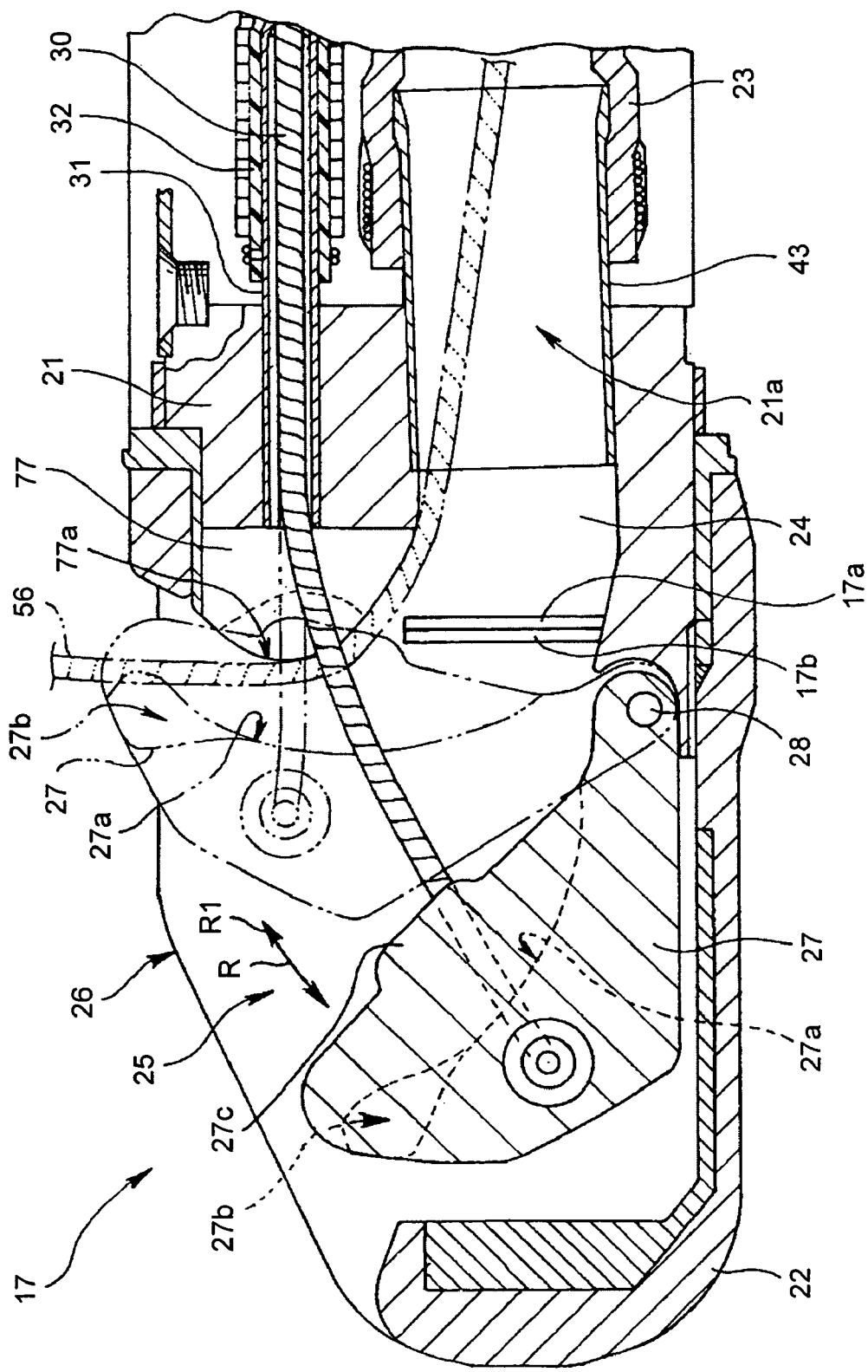
FIG. 3 is a sectional view along line III-III of FIG. 2.
Figure 4:
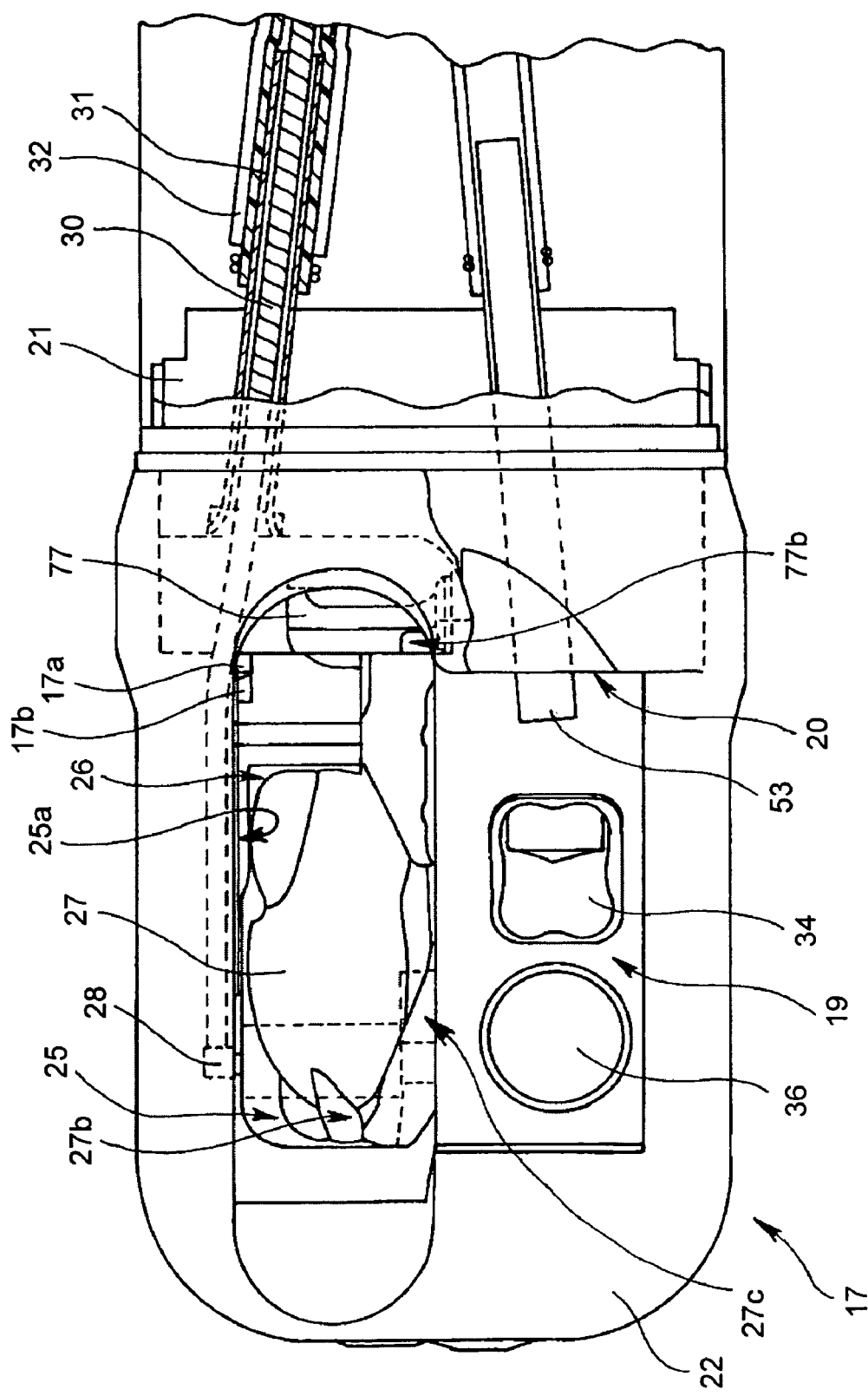
FIG. 4 is a top view of the distal end portion of the endoscope of FIG. 1.
Figure 5:
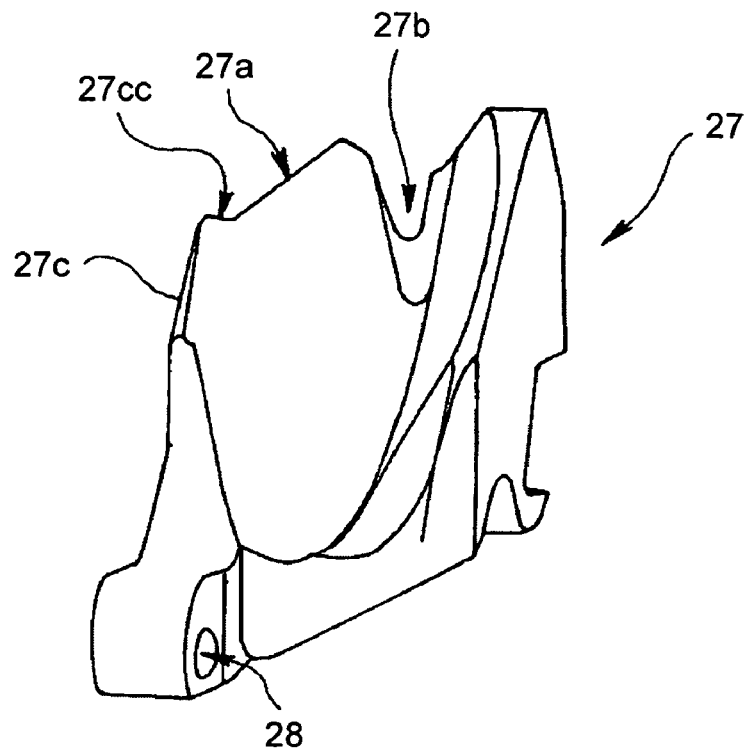
FIG. 5 is a perspective view of a treatment instrument raiser alone of the endoscope of FIG. 1.
Figure 6:
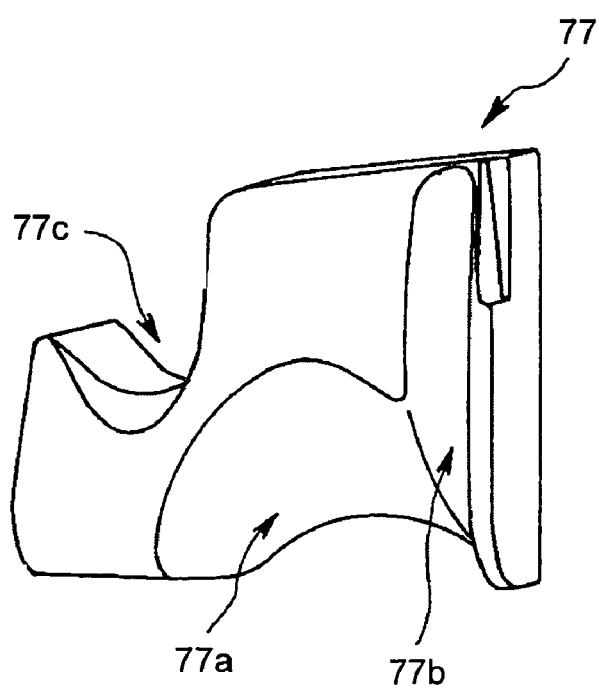
FIG. 6 is a perspective view of a portion of an insulating member of the endoscope of FIG. 1.

FIG. 1 is a perspective view showing a schematic structure of an endoscopic system including an endoscope according to an embodiment of the present invention. FIG. 2 is an enlarged perspective view of a relevant portion of a distal end portion of the endoscope of FIG. 1. FIG. 3 is a sectional view along line III-III of FIG. 2. FIG. 4 is a top view of the distal end portion of the endoscope of FIG. 1. In FIG. 4, a guide wire is not shown. FIG. 5 is a perspective view of a treatment instrument raiser alone of the endoscope of FIG. 1. FIG. 6 is a perspective view of a portion of an insulating member of the endoscope of FIG. 1.

Prior to a detailed description of the endoscope of the present embodiment, a schematic overall structure of the endoscopic system including the endoscope will be described below mainly with reference to FIG. 1.

As shown in FIG. 1, an endoscopic system 100 includes an endoscope 1 of the present embodiment and a peripheral device 50 thereof. The endoscope 1 mainly includes an operation portion 13, an insertion portion 12, and a universal cord 14. An insertion portion protecting member 33 is arranged to protect the insertion portion 12 at a position where the insertion portion 12 and the operation portion 13 are connected.

The peripheral device 50 mainly includes various devices arranged on a counter 9 to which casters 8 are attached at a bottom portion. The peripheral device 50 includes, for example, a light source 2, a video processor 3, a monitor 4, a keyboard 5, a suction pump device 6, and a water delivery bottle 7. Further, the light source 2 and the video processor 3 are electrically connected via a connecting cable 73. Further, the endoscope 1 and the peripheral device 50 are connected by a connector 18.

The connector 18 is connected to the light source 2 of the peripheral device 50. The connector 18 has a ferrule (not shown) which forms an end of a fluid pipe, a light guide ferrule (not shown) which forms an end of a light guide, and an electrical contact (not shown). The light guide extends from the universal cord 14, penetrates through the operation portion 13 and the insertion portion 12, and reaches the distal end portion 17 of the insertion portion 12. Thus, illumination light emitted from the light source 2 is emitted from an illumination lens 36 (see FIGS. 2 and 4) of the distal end portion 17 toward an interior of a body cavity in a radially expanded manner.

In the operation portion 13 of the endoscope 1, a bending operation knob 35, an air/water delivery operation button 37, a suction operation button 38, a treatment instrument raiser operation knob (hereinafter simply referred to as operation knob) 48 which is employed for a raising operation of a treatment instrument raiser 27 (described in detail later; see FIGS. 3 and 5), and a treatment instrument insertion port 40 which has an opening 40a through which a predetermined treatment instrument is inserted into a treatment instrument insertion channel 23 (see FIG. 3) arranged inside the insertion portion 12 of the endoscope 1 are provided.

The insertion portion 12 of the endoscope 1 includes a distal end portion 17, a bendable portion 16, and a flexible tube portion 15. The bendable portion 16 is manipulated so as to bend via the bending operation knob 35 provided in the operation portion 13, and is arranged between the distal end portion 17 and the flexible tube portion 15.

A portion of an outer circumference of the distal end portion 17 is removed to form a cut out portion 19 having a depressed shape, and a channel opening 26 which is located at a distal end side of the treatment instrument insertion channel 23 (see FIG. 3) is provided on a surface of the cut out portion 19.

Further, an objective lens 34 of an imaging unit (not shown) housed in the distal end portion 17 and an illumination lens 36 of an illumination optical system are arranged near the channel opening 26 in the cut out portion 19 (see FIGS. 2 and 4).

Further, a nozzle 53 for air and water delivery is projected from a wall surface 20 at a back end side of the cut out portion 19 of the distal end portion 17. When a fluid such as water and air is to be sprayed toward an outer surface of the objective lens 34 for cleaning of the objective lens 34 through an operation of the air/water delivery operation button 37 of the operation portion 13, the fluid is ejected from the nozzle 53.

A treatment instrument raiser housing chamber (hereinafter simply referred to as housing chamber) 25 is formed near the channel opening 26 in the distal end portion 17. In the housing chamber 25, the treatment instrument raiser 27 which serves to raise the treatment instrument (not shown) or a guide wire 56 is arranged.

The treatment instrument raiser 27 is driven according to a rotation operation of the operation knob 48 via a raising wire 30 (see FIGS. 3 and 4) which is driven in conjunction with a holder engaging/driving mechanism (not shown) provided inside he operation portion 13. When the treatment instrument raiser 27 is driven, the direction of advance (axial direction of the insertion portion 12) of the treatment instrument or the guide wire 56, which enters the treatment instrument insertion channel 23 from the opening 40a of the treatment instrument insertion port 40 to stick out from the channel opening 26, inside the treatment instrument insertion channel 23 is changed to a direction of the channel opening 26. The treatment instrument raiser 27 is configured to rise to a maximum extent to secure the guide wire 56 when the treatment instrument is to be withdrawn from the pancreatic duct, bile duct, hepatic duct, or the like.

The guide wire 56 is an elongated linear member including a core wire of a superelastic allow, for example, and a soft outer cladding of Teflon® or urethane, for example, which covers the core wire. The guide wire 56 is inserted into the pancreatic duct, bile duct, hepatic duct, or the like before the insertion of the treatment instrument (not shown) when the treatment instrument such as a forceps and catheter is to be inserted into an extremely thin duct, such as the pancreatic duct, bile duct, hepatic duct, or the like, in the body cavity with the use of the endoscope 1, and thereby the guide wire 56 works as a guiding member for the insertion of the treatment instrument.

In the following, an inner structure of the distal end portion 17 of the endoscope 1, in particular, the structure of the treatment instrument raiser 27, will be described schematically mainly with reference to FIG. 3.

As shown in FIG. 3, the distal end portion 17 of the endoscope 1 includes a distal end hard portion 21, which serves as a main body of the distal end portion, and a distal end cover 22 which is made of a non-conductive material such as resin and arranged so as to cover the distal end hard portion 21. The distal end cover 22 is bonded and secured to the distal end hard portion 21 at a distal end side of the distal end hard portion 21 by a bonding agent or the like.

In the distal end hard portion 21, an elongated hole 21a is formed along the insertion direction. A connecting pipe 43 which serves as a guiding path for the insertion of the treatment instrument (not shown) fits into the elongated hole 21a. A distal end portion of the treatment instrument insertion channel 23, through which the treatment instrument is inserted, is fixed around an outer circumference of the connecting pipe 43 at the back end side of the connecting pipe 43. At a distal end side of the connecting pipe 43, an introduction guiding path 24, which guides the treatment instrument or the guide wire 56 inserted into the treatment instrument insertion channel 23 through the connecting pipe 43 to a side of the channel opening 26, is formed.

At a distal end side of the introduction guiding path 24, the housing chamber 25 is formed as a space surrounded by the distal end hard portion 21 and the distal end cover 22. The housing chamber 25 has an opening at a top surface side. The opening serves as the channel opening 26 which forms a distal end opening of the treatment instrument insertion channel 23.

In an inside space of the housing chamber 25, the treatment instrument raiser 27 is arranged. The treatment instrument raiser 27 is substantially triangular in section, and one end thereof is rotatably supported at a holder rotation support point 28 which serves as an axis and is formed at a position close to a bottom surface of the distal end hard portion 21 near the distal end opening of the introduction guiding path 24. Thus, the treatment instrument raiser 27 can rotate within a predetermined range within the housing chamber 25 in a direction of arrow R shown in FIG. 3.

The treatment instrument raiser 27 has a treatment instrument guiding surface 27a in a position opposite to the channel opening 26. The treatment instrument guiding surface 27a is a groove with a substantially V-shaped section communicating with the introduction guiding path 24 and serves to guide the treatment instrument toward the channel opening 26.

On a distal end side of the treatment instrument guiding surface 27a, a slit 27b which is substantially V shape (see FIGS. 4 and 5) is formed. When the treatment instrument raiser 27 is raised by a predetermined operation, the guide wire 56 fits into the slit 27b and secured therein.

In a middle position on a side surface of the treatment instrument raiser 27, one end of a raising wire 39 is connected. The raising wire 30 extends from the holder engaging/driving mechanism (not shown) of the operation portion 13 and penetrates through the insertion portion 12. An outer circumference of the raising wire 30 is covered with a guide pipe 31, which runs inside a guide tube 32 penetrating the insertion portion 12.

The treatment instrument raiser 27 is raised by rotating around the holder rotation support point 28 according to the traction operation of the raising wire 30. The treatment instrument raiser 27 is configured so as to rise up to a position regulated by a first stopper portion 17a described later. In the description, the position where the treatment instrument raiser 27 is held by the first stopper portion 17a is referred to as a maximum rising position.

An insulating member 77 is arranged at a position facing the treatment instrument raiser 27 at a distal end side of the distal end hard portion 21.

Further, as shown in FIG. 6, a depressed guiding surface 77a is formed on a surface of the insulating member 77 at a distal end side so that the guiding surface 77a opens toward a front side. The guiding surface 77a and the slit 27b of the treatment instrument raiser 27 sandwich the guide wire 56 when the treatment instrument raiser 27 is arranged at the maximum rising position. Then, the guide wire 56 bites into the slit 27b, and is secured so as not to move in the axial direction.

The position of the treatment instrument raiser 27 is regulated by a second stopper portion 17b described later so that the treatment instrument raiser 27 does not move farther than a predetermined position slightly forward from the maximum rising position. The insertion operation of the treatment instrument is performed while the treatment instrument raiser 27 is in the above position. Thus, the insulating member 77 and the treatment instrument raiser 27 are set and arranged so that the treatment instrument and the guide wire 56 can move in both the direction of insertion and the direction of withdrawal between the guiding surface 77a of the insulating member 77 and the guiding surface 27a of the treatment instrument raiser 27.

Further, a retraction slit portion 77b is formed near the guiding surface 77a of the insulating member 77, so that a guide wire guiding portion 27c (described later) of the treatment instrument raiser 27 can fit into the retraction slit portion 77b to prevent interference when the treatment instrument raiser 27 is raised to the maximum rising position. Thanks to the retraction slit portion 77b, the treatment instrument raiser 27 can surely rise to the maximum rising position (position of the first stopper portion 17a) over an angle required for rising.

Further, a U-shaped groove 77c having a U-shaped section and opens upward is formed on a side edge portion of the insulating member 77. The raising wire 30 is slidably arranged in the U-shaped groove 77c.

On an outer periphery of the treatment instrument guiding surface 27a of the treatment instrument raiser 27, a guide wire guiding portion 27c is formed as means for guiding the guide wire. The guide wire guiding portion 27c holds the guide wire 56 on the treatment instrument guiding surface 27a so that the guide wire 56 does not fall off from the treatment-instrument guiding surface 27a and guides the guide wire 56 to the slit 27b when the guide wire 56 is raised by the treatment instrument raiser 27. The guide wire guiding portion 27c is a protrusion formed at a portion of the outer periphery of the treatment instrument guiding surface 27a adjacent to the housing chamber 25, and has a substantially trapezoidal section and is projected outward at a predetermined position on a side surface of the treatment instrument raiser 27 at a side adjacent to a fixing member on which the illumination lens 36 or the like is arranged.

On a predetermined position of the inner wall of the housing chamber 25, a rising range regulating mechanism for the treatment instrument raiser 27 is arranged. The rising range regulating mechanism includes a stopper driving mechanism 47 which includes the second stopper portion 17b regulating the rising of the treatment instrument raiser 27 at a predetermined position, and the first stopper portion 17a regulating the maximum rising position of the treatment instrument raiser 27.

The first stopper portion 17a is projected from a side wall 25a near the proximal end of the housing chamber 25 so as to protrude inwardly as shown in FIG. 4. Near the first stopper portion 17a, the second stopper portion 17b which is arranged so as to be able to protrude and retract on the side wall 25a and the stopper driving mechanism 47 which realizes the protruding/retracting operation of the second stopper portion 17b.

Figure 7:
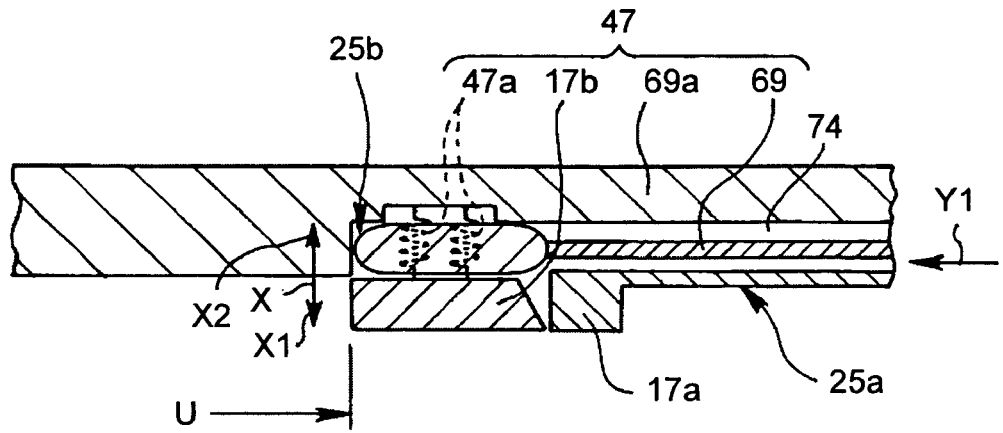
FIG. 7 is a diagram of a rising range regulating mechanism in the endoscope of FIG. 1 in a normal state where a second stopper portion is projected.
Figure 8:
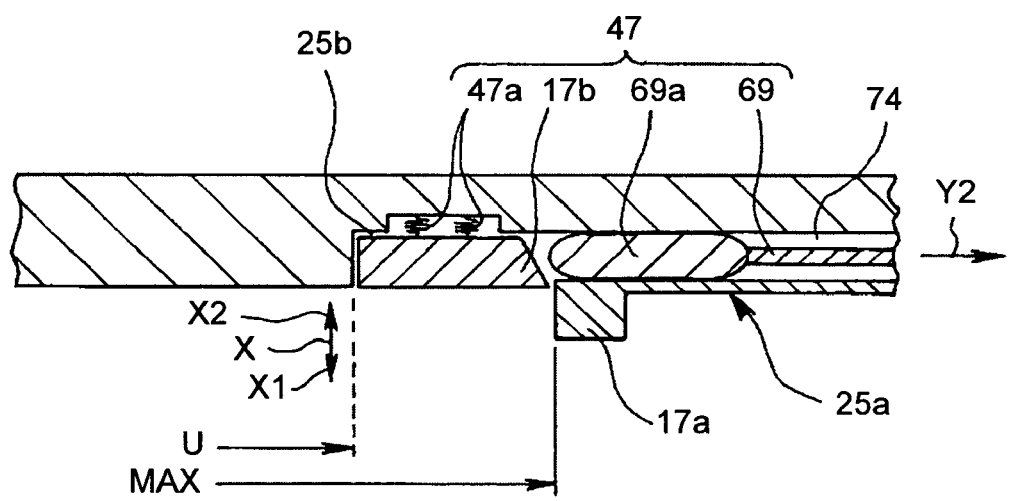
FIG. 8 is a diagram of the rising range regulating mechanism of FIG. 7 in a state where the second stopper portion is housed in an inner wall and a maximum rising position of the treatment instrument raiser is regulated by a first stopper portion.

The first stopper portion 17a and the second stopper portion 17b are shown in detail in FIGS. 7 and 8. FIG. 7 shows the second stopper portion 17b in a normal state, i.e., a protruding state. FIG. 8 shows the second stopper portion 17b housed in the inner wall in a retracted state, where the maximum rising position of the treatment instrument raiser 27 is regulated by the first stopper portion 17a.

The second stopper portion 17b is configured so as to be able to retract and protrude, taking the position in the side wall 25a (state shown in FIG. 8) or the position protruding toward inside the housing chamber 25 from the side wall 25a (state shown in FIG. 7).

A housing portion 25b is formed so as to house the second stopper portion 17b in the side wall 25b. On a bottom surface of the housing portion 25b, a tension elastic member 47a is arranged. The second stopper portion 17b is supported by the elastic member 47a. While the second stopper portion 17b is in a normal state, the second stopper potion 17b is constantly biased in a direction of arrow X2 shown in FIGS. 7 and 8 by the elastic member 47.

On the other hand, a traction wire channel 74 through which the traction wire 69 is inserted is communicated with the housing portion 25b. The traction wire channel 74 is communicated with a predetermined position inside the operation portion 13 via the interior of the insertion portion 12 of the endoscope 1. The traction wire 69 runs through the traction wire channel 74. On a distal end of the traction wire 69, a distal end member 69a is fixed. The distal end member 69a moves and makes the second stopper portion 17b protrude in a direction against the biasing force of the elastic member 47a (direction of arrow X1 in FIGS. 7 and 8) when the traction wire 69 is pushed in a direction of arrow Y1 of FIG. 7 by the stopper driving mechanism 47 described later. In other words, when the traction wire 69 is pushed, the distal end member 69a comes inside the housing portion 25b, thereby pushing out the second stopper portion 17b. To facilitate the above motion, a back end side portion of the second stopper portion 17b, i.e., an end surface, with which the distal end member 69a is brought into contact, of the second stopper portion 11b is formed so as to be inclined relative to a direction of motion (direction of insertion) of the traction wire 69.

Thus, the second stopper potion 17b is arranged so as to protrude toward inside the housing chamber 25 from the side wall 25a as shown in FIG. 7. The state shown in FIG. 7 is the normal state of the endoscope 1.

When the second stopper potion 17b is in the position of FIG. 7, and the treatment instrument raiser 27 rises, a part of the treatment instrument raiser 27 is brought into contact with the second stopper portion 17b. Then, a further rotation (in a direction of arrow R1 of FIG. 3) of the treatment instrument raiser 27 is prevented.

On the other hand, when the traction wire 69 is pulled by the stopper driving mechanism 47 in a direction of arrow Y2 of FIG. 8, the distal end member 69a is pulled out from the housing portion 25b. Then, the second stopper portion 17b in the state of FIG. 7 (protruding state) moves in a direction to retract inside the housing portion 25b (direction of arrow X2 of FIGS. 7 and 8) according to the biasing force of the elastic member 47a. Thus, the second stopper portion 17b comes to be arranged in a retracted position inside the housing portion 25b in the side wall 25a as shown in FIG. 8.

While the second stopper portion 17b is at the position of FIG. 8, a portion of the treatment instrument raiser 27 passes by the second stopper portion 17b and rotates further until coming into contact with the first stopper portion 17a. Thus, the maximum rising position (see, e.g., position shown by a chain line in FIG. 3) of the treatment instrument raiser 27 is regulated.

A part of the stopper driving mechanism 47 is arranged at a side of the operation portion 13. Among elements of the stopper driving mechanism 47, elements (operation members and the like) arranged at the side of the operation portion 13 will be described with reference to FIGS. 9 to 11.

Figure 9:
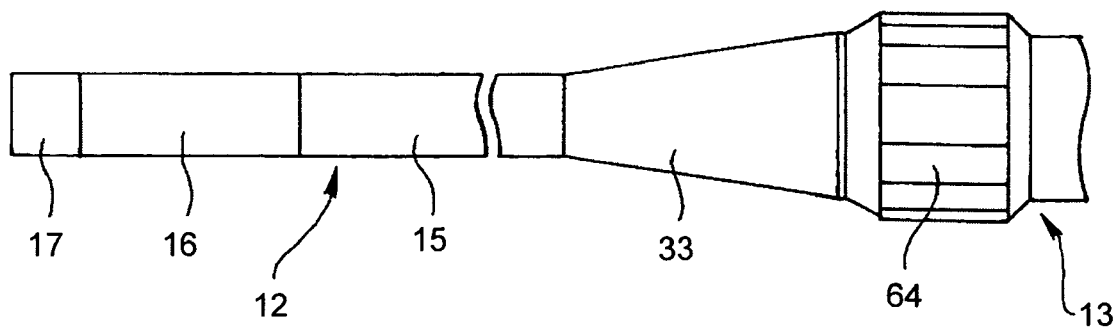
FIG. 9 is an enlarged plan view of a relevant portion of a stopper driving mechanism which is a part of the rising range regulating mechanism in the endoscope of FIG. 1, and shows a portion around a position where an operation knob is arranged.
Figure 10:
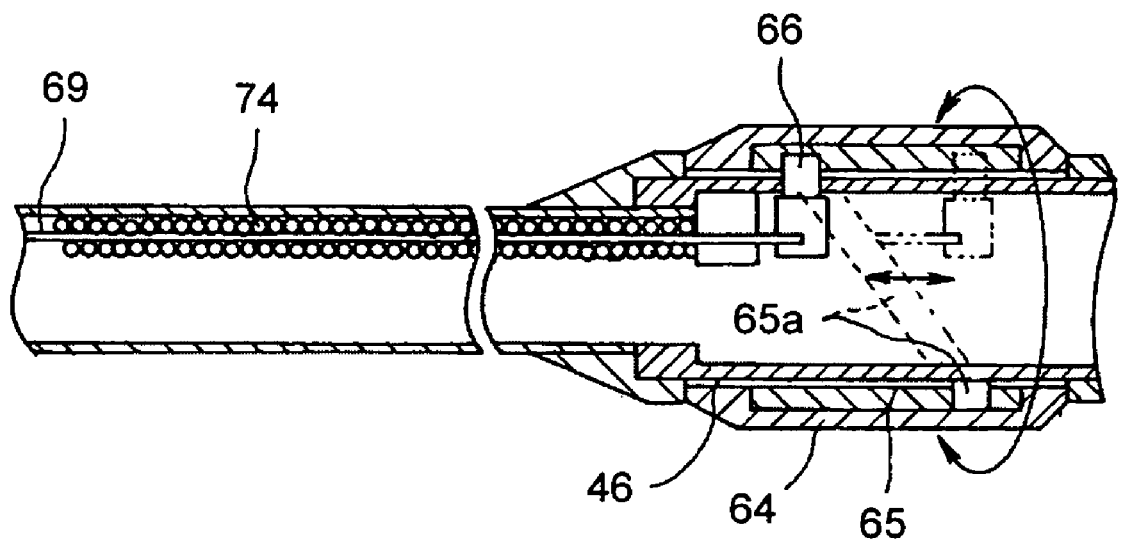
FIG. 10 is a vertical sectional view of an internal structure of the portion of FIG. 9.
Figure 11:
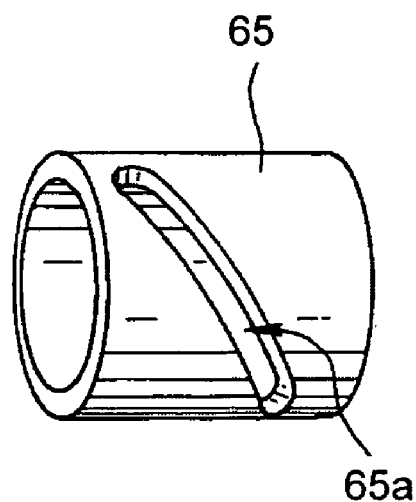
FIG. 11 is an enlarged perspective view of a cam member which is a part of the stopper driving mechanism of FIG. 9.

FIG. 9 is an enlarged plan view of a relevant portion of the stopper driving mechanism, in particular a portion around the position where the operation knob is arranged in the stopper driving mechanism which is a part of the operation portion 13. FIG. 10 is a vertical sectional view of an internal structure of the portion of FIG. 9. FIG. 11 is an enlarged perspective view of a cam member which is a part of the stopper driving mechanism.

As shown in FIGS. 1 and 9, the operation portion 13 of the endoscope 1 of the present embodiment has a substantially cylindrical traction knob 64 which is an operation member for the traction operation of the traction wire 69. The traction knob 64 is arranged between a grip 62 by which the operator grips the operation portion 13 and the insertion portion protecting member 33. The traction knob 64 is rotatably attached to an internal securing member 46 of the operation portion 13 as shown in FIG. 10. Further, an axis of rotation of the traction knob 64 is arranged so as to be aligned with a central axis of the insertion portion 12 of the endoscope 1.

A cylindrical cam member 65 (see FIGS. 10 and 11) is integrally arranged inside the traction knob 64. On a circumference of the cam member 65, a cam groove 65a is curbed askew as shown in FIGS. 10 and 11. A moving pin 66 engages with the cam groove 65a as shown in FIG. 10. Thus, when the cam member 65 rotates, the moving pin 66 moves in a direction along the central axis of the insertion portion 12 and the traction knob 64. A proximal end of the traction wire 69, which is inserted inside the traction wire channel, is fixed to the moving pin 66. When the traction knob 64 is rotated, the cam member 65 is rotated accordingly. Then, the moving pin 66 moves along the cam groove 65a of the cam member 65.

Thus, the traction wire 69 proceeds and retracts along the axial direction of the insertion portion 12 according to the movement of the moving pin 66. As described above, the distal end member 69a is fixed to the distal end of the traction wire 69. When the traction wire 69 proceeds or retracts, the distal end member 69a follows the movement of the traction wire 69.

Thus, a position where the rotation of the treatment instrument raiser 27 can be set at any time by rotating the traction knob 64 and setting the second stopper portion 17b at a desired position. For example, if the operator rotates the traction knob 64 to push the traction wire 69 to bring it in the state shown in FIG. 7, the range of rotation of the treatment instrument raiser 27 comes to be regulated by the second stopper portion 17b. The range of rotation of the treatment instrument raiser 27 is delimited by a position where the treatment instrument raiser 27 comes into contact with the second stopper portion 17b, i.e., a position shown by U in FIG. 7.

On the other hand, if the operator rotates the traction knob 64 while the traction wire 69 is in the state of FIG. 7 so as to pull the traction wire 69 in a direction of traction and bring the traction wire in the state shown in FIG. 8, the range of rotation of the treatment instrument raiser 27 comes to be regulated by the first stopper portion 17a. Then, the range of rotation of the treatment instrument raiser 27 is delimited by a position where the treatment instrument raiser 27 comes into contact with the first stopper portion 17a, i.e., a position shown by MAX (maximum rising position) in FIG. 8. In other words, in this case, the treatment instrument raiser 27 can be raised further by a predetermined amount from the position shown by U in FIG. 7.

The treatment instrument raiser 27 is configured so that the treatment instrument raiser 27 can be raised through the traction of the raising wire 30 (see FIGS. 3 and 4) via the holder engaging/driving mechanism (not shown) provided inside the operation portion 13 when the operation knob 48 in the operation portion 13 is rotated. The operation knob 48 is arranged at a predetermined position in the operation portion 13 as shown in FIG. 12.

Figure 12:
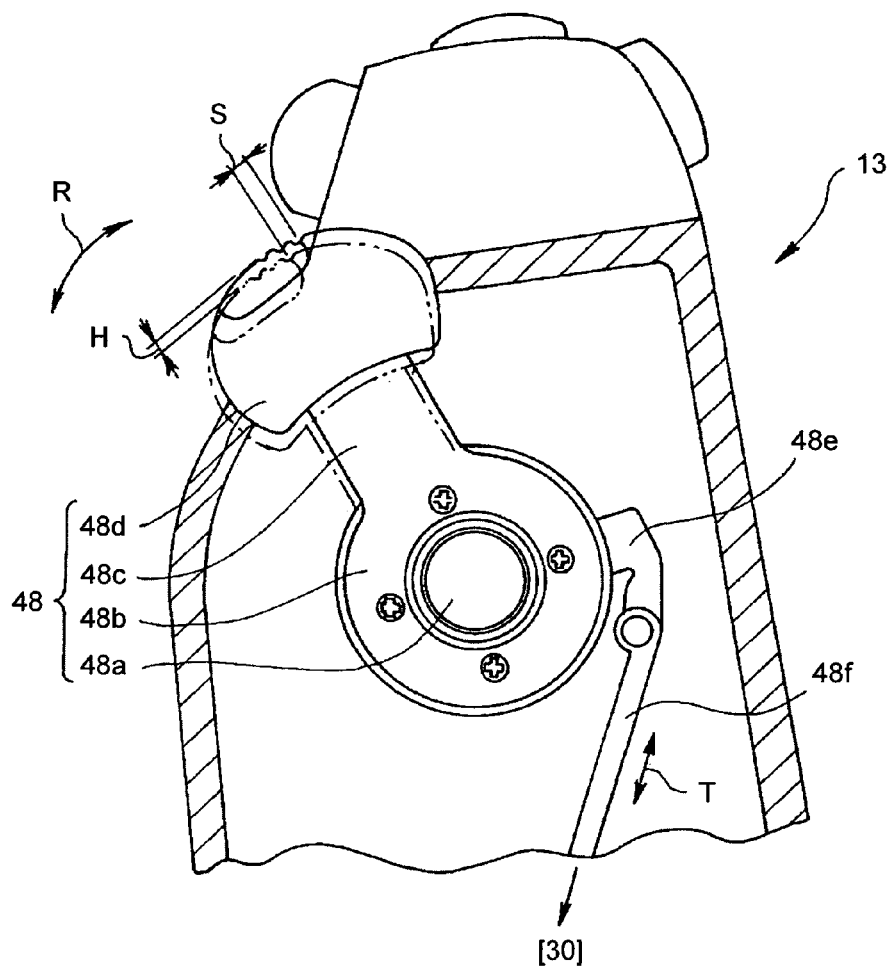
FIG. 12 is an enlarged view of a relevant portion of a part of an operation portion of the endoscope of FIG. 1, and shows an arrangement of an operation knob provided in the operation portion.

FIG. 12 is an enlarged view of a relevant portion of a part of the operation portion of the endoscope of the present embodiment and shows an arrangement of the operation knob provided in the operation portion. In FIG. 12, members other than the operation knob in the operation portion are not shown for the simplicity of description.

The operation knob 48 is arranged so as to be rotatable around an axial portion 48a arranged perpendicular to the axial direction of the operation portion 13, and is arranged on a side surface of the operation portion 13. The operation knob 48 is a lever-like operation member which includes the axial portion 48a, a proximal end portion 48b fixed to one end of the axial portion 48a, an arm 48c which extends from the proximal end portion 48b, and a knob portion 48d which is integrally arranged at a distal end of the arm 48c. When the operator puts a finger on the knob portion 48d and moves the knob portion 48d in a direction of arrow R shown in FIG. 12, the operator can rotate the operation knob 48. Along with the rotation of the operation knob 48, the lever portion 48e formed on an outer circumference of the proximal end portion 48b rotates. Then, a link member 48f connected to the lever portion 48e moves in a direction of arrow T of FIG. 12. To the link member 48f, a raising wire 30 is connected. Accordingly, the raising wire 30 can be pulled.

In the endoscope 1 of the present embodiment, when the treatment instrument raiser 27 is raised to the maximum rising position, the guide wire 56 is held between the slit 27b of the treatment instrument raiser 27 and the guiding surface 77a of the insulating member 77, and at the same time the slit 27b is made to bite into the guide wire 56, whereby a high securing strength is obtained.

Here, the securing strength of the guide wire 56 while the treatment instrument raiser 27 is at the maximum rising position can be adjusted by the amount of rising of the treatment instrument raiser 27, i.e., a rising stroke. An easy and effective way to improve the securing strength of the guide wire 56 by the slit 27b is to increase an amount of rising angle of the treatment instrument raiser 27. In other words, the increased angle of rotation of the operation knob 48 is sufficient to increase the rising angle of the treatment instrument raiser 27 and to increase the rising range of the treatment instrument raiser 27.

For the above mentioned purpose, in the operation knob 48 of the present embodiment, a dimension of a length of the arm of the operation knob 48 (dimension from a center of the axial portion 48a to a top of the knob portion 48d; also referred to as a height dimension of the operation knob 48) is made slightly longer than that in a conventional member. The operation knob 48 is configured so that the height dimension of the operation knob 48 shown by a solid line in FIG. 12 is longer than that of the conventional operation knob 48 shown by a chain line in FIG. 12. Specifically, the operation knob 48 of the embodiment is longer than that of the conventional one by approximately 1 mm as indicated by character H in FIG. 12. Thus, the amount of rotation of the operation knob 48 can be made larger than that of the conventional one by an amount indicated by character S in FIG. 12.

To increase the height dimension of the operation knob 48, it is desirable that the position of the top of the knob portion 48d of the operation knob 48 be placed on a rotation arc of the bending operation knob 35 or within a radius of rotation of the bending operation knob 35, for example, so that the operability will not be degraded.

The increase of the height dimension of the operation knob 48 does not require a drastic change in design, and still a desirable rising stroke can be obtained.

The treatment instrument raiser 27 can be employed also to raise the treatment instrument that has a tube sheath such as a cannula (not shown in particular) and to direct a distal end thereof in a desired direction when such a treatment instrument is to be inserted into a desired duct such as the pancreatic duct, bile duct, and hepatic duct. When the treatment instrument raiser 27 is erroneously raised up to the maximum rising position to raise the treatment instrument, the treatment instrument might be buckled.

To deal with the above inconveniences, the treatment instrument may have a following structure.

Figure 13:
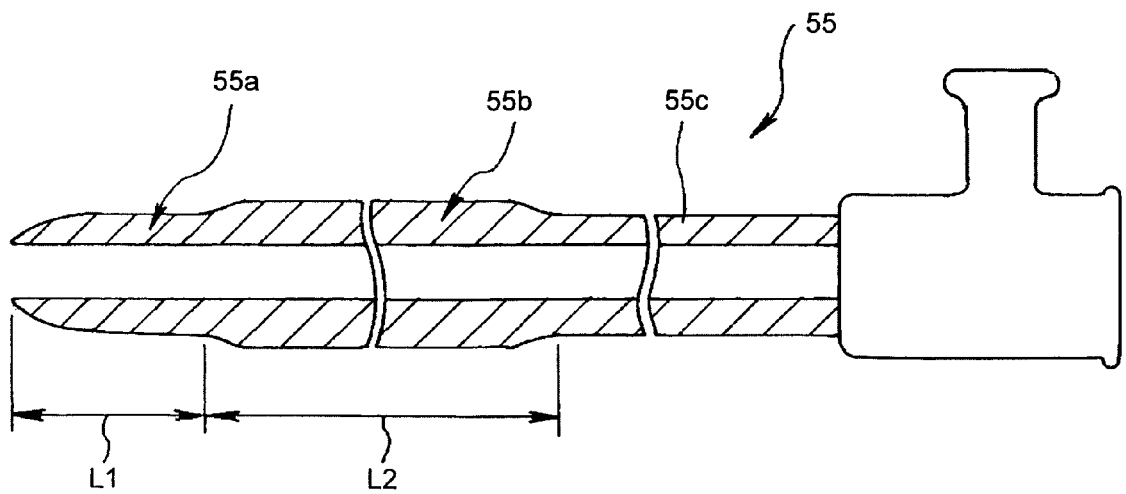
FIG. 13 is a schematic sectional view of a schematic structure of a treatment instrument which is configured so as to prevent buckling and which corresponds to the endoscope of FIG. 1.
Figure 14:
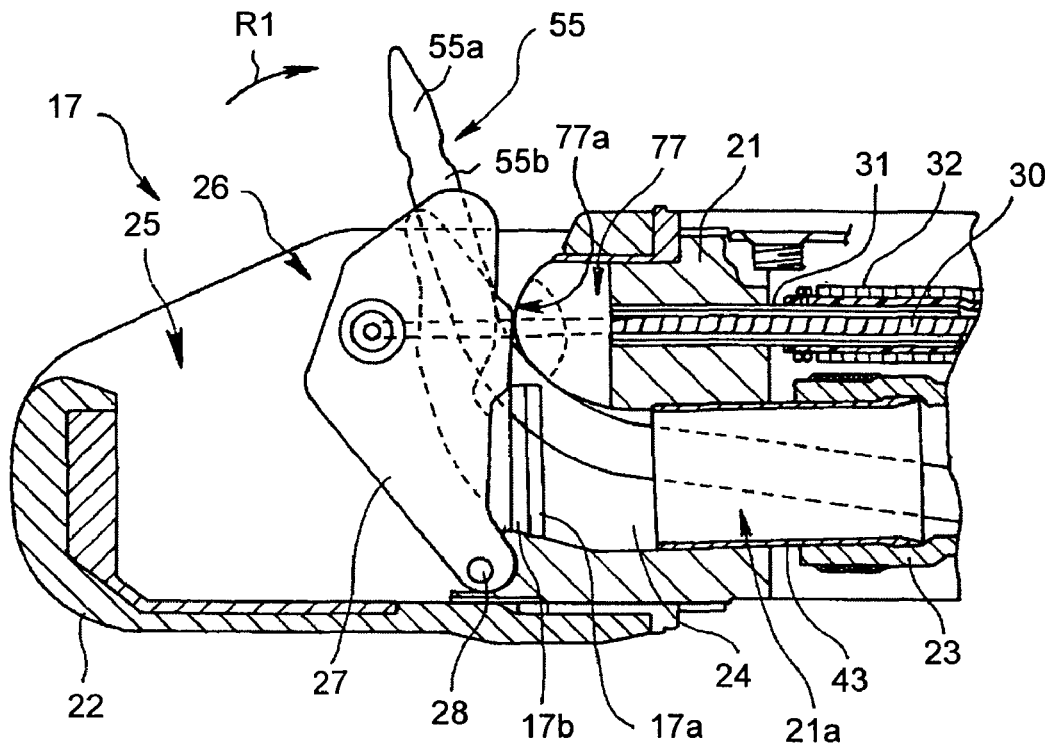
FIG. 14 is an enlarged sectional view of a portion around the distal end portion of the endoscope, which shows the treatment instrument of FIG. 13 applied to the endoscope of FIG. 1.

FIG. 13 is a schematic sectional view of a schematic structure of a treatment instrument which is configured so as to prevent buckling and which corresponds to the endoscope of the present embodiment. FIG. 14 is an enlarged sectional view of a portion around the distal end portion of the endoscope, and shows the treatment instrument of FIG. 13 applied to the endoscope of the present embodiment.

As shown in FIG. 13, a treatment instrument 55 corresponding to the endoscope 1 of the present embodiment has a tube sheath such as a cannula. The treatment instrument 55 is supposed to have three regions, i.e., a distal end region 55a which is a predetermined region near the distal end, a thick region 55b which is connected to the distal end region 55b and which is configured to be slightly thick, and a proximal end region 55c which is connected to the thick region 55b and arranged near the proximal end. The distal end region 55a is, for example, a region having a dimension L1 from a most distal end portion as shown in FIG. 13 (more specifically, L1 is approximately 20 to 30 mm). The thick region 55b is a region connected to the distal end region 55a and has a dimension L2 (specifically approximately 200 mm) as shown in FIG. 13, for example. The proximal end region 55c covers all area extending from an edge of the thick region 55b to the proximal end.

Here, thickness of the tube in the treatment instrument 55 is substantially the same in the distal end region 55a and the proximal end region 55c, while the thickness in the thick region 55b is slightly increased than that in the other two regions. An inner diameter of the treatment instrument 55 is made to be identical from a distal end up to a proximal end. Thus, the insertability of the guide wire 56 and the flowability of the contrast agent are maintained.

The thick region 55b of the treatment instrument 55 has a high probability of contacting with the insulating member 77 during the guiding of the distal end of the treatment instrument 55 through the channel opening 26 of the endoscope 1 as shown in FIG. 14. In other words, the region is a portion where the force is applied when the treatment instrument raiser 27 raises the treatment instrument. That is why the portion is made to be thicker. Thus, the treatment instrument 55 rarely buckles even when the treatment instrument raiser 27 is raised.

Meanwhile, in the endoscopic system 100 to which the endoscope 1 of the present embodiment is applied, a following display is presented on the screen of the monitor 4 during the rising operation of the treatment instrument raiser 27 in order to prevent the treatment instrument raiser 27 from causing the buckling and the damages of the treatment instrument 55.

Figure 15:
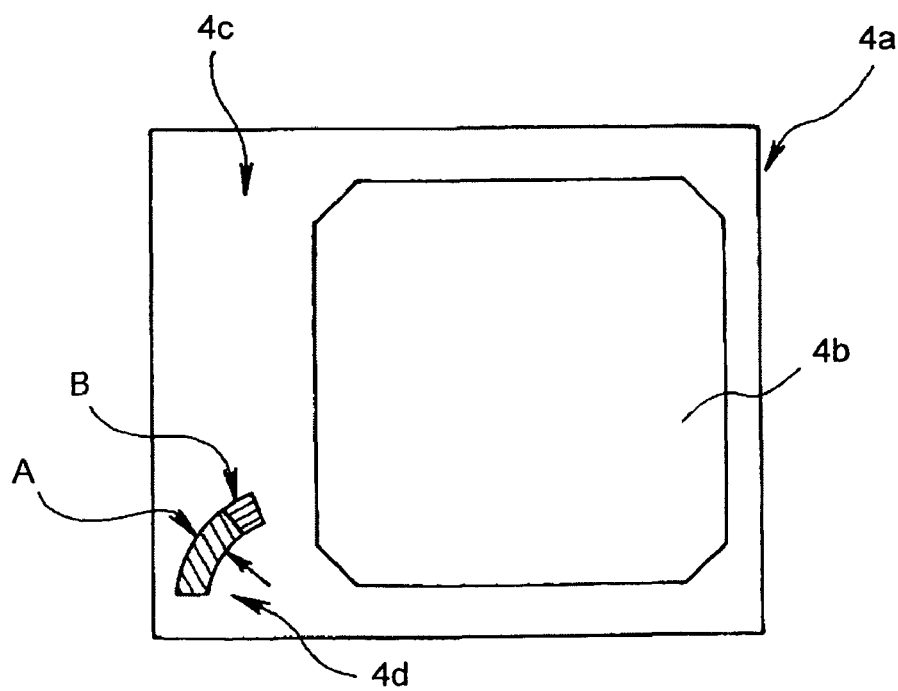
FIG. 15 is a diagram of an example of a display screen of a monitor in an endoscopic system to which the endoscope of FIG. 1 is applied.

FIG. 15 is a diagram of an example of a display screen of the monitor in the endoscopic system to which the endoscope of the present embodiment is applied.

As shown in FIG. 15, an information display region 4c is presented on the display screen 4a of the monitor 4 so as to display various types of information in addition to an endoscopic image 4b. The information display region 4c has a predetermined region 4d whose display indicates a rising state of the treatment instrument raiser 27 during the raising operation.

FIG. 15 is an example of the display. In the example of FIG. 15, there is a graph-like indication of a substantially circular arc shape. In the graph-like indication, a region indicated by character A is shown in green, while a region indicated by character B is shown in red. A detecting unit such as a position sensor provided near the treatment instrument raiser 27 detects an amount of rising of the treatment instrument raiser 27, and the display is given in a predetermined manner based on the detected amount.

In the example shown in FIG. 15, the graph-like indication is shown. The present invention is not limited thereto. Alternatively, a number representing the rising angle may be displayed together, or the numbers alone may be displayed.

The detecting unit is desirably provided near the treatment instrument raiser 27. The detecting unit, however, can be provided inside the operation portion 13, for example. In this case, the detecting unit may be configured to detect a travel amount of the raising wire 30, for example, or to detect an amount of rotation of the operation knob 48 or the like.

A function of the endoscope 1 of the present embodiment having the above mentioned structure will be described below. More specifically, an operation at the time of raising operation according to which the guide wire 56 is raised via the operation knob 48 (see FIG. 1) and an operation at a fixing operation according to which the guide wire 56 is secured at a predetermined position will be described below.

Figure 16:
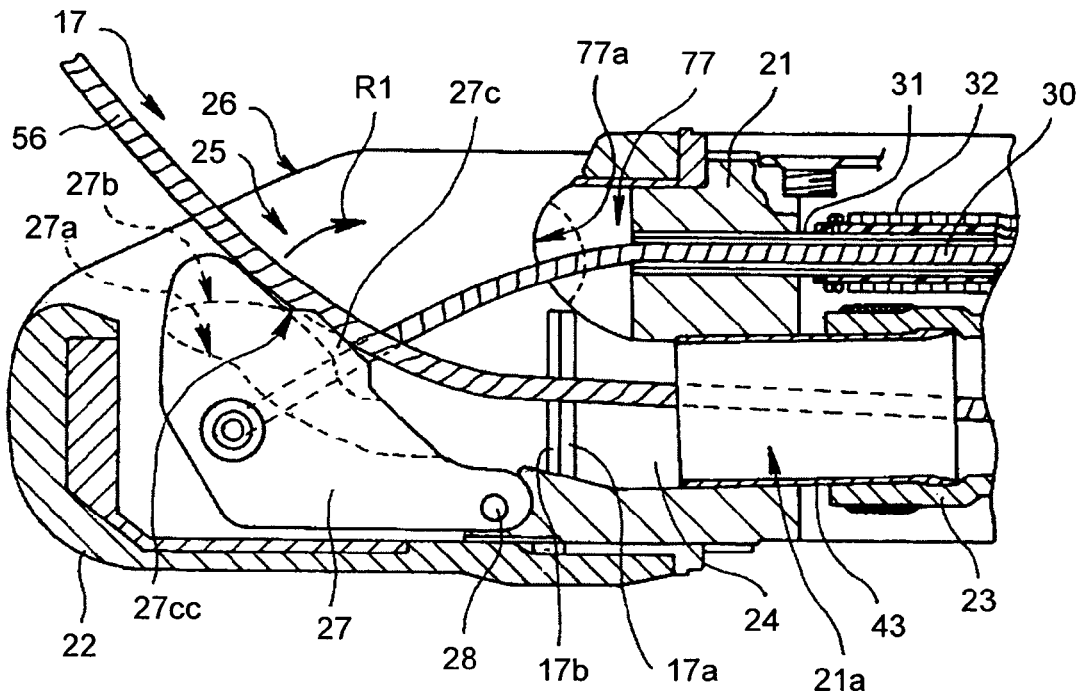
FIG. 16 is a sectional view along line III-III of FIG. 2, provided to described a function in the endoscope of FIG. 1 during a raising operation, and shows the distal end portion of the endoscope in an initial state.
Figure 17:
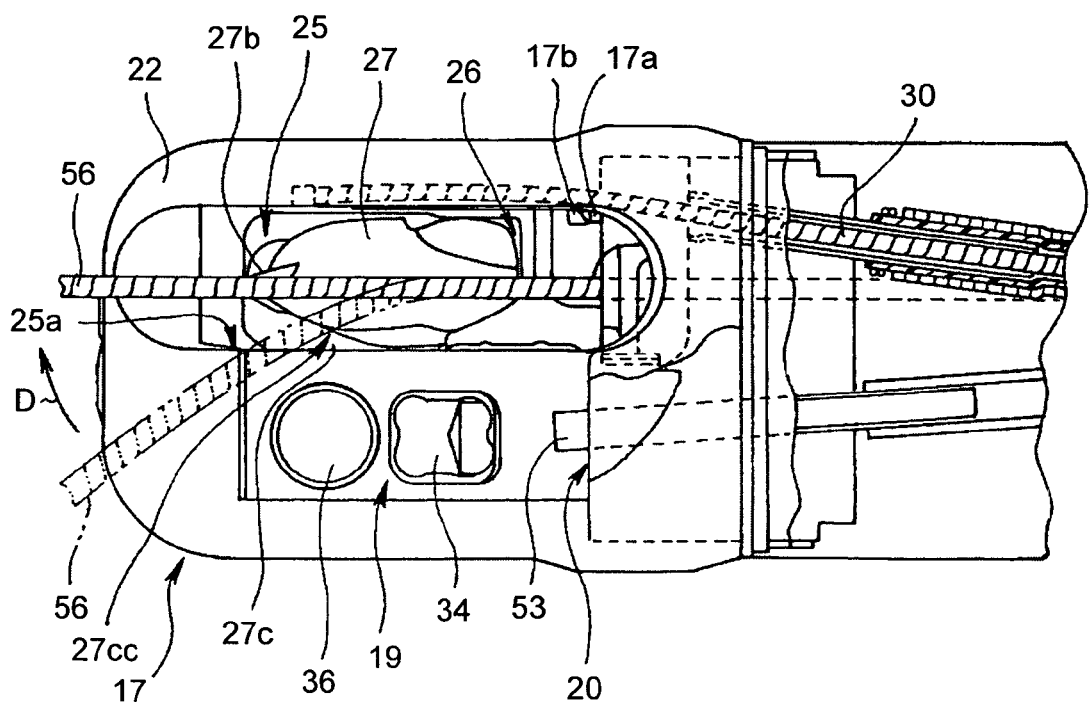
FIG. 17 is a top view of the distal end portion of the endoscope in the initial state of FIG. 16.
Figure 18:
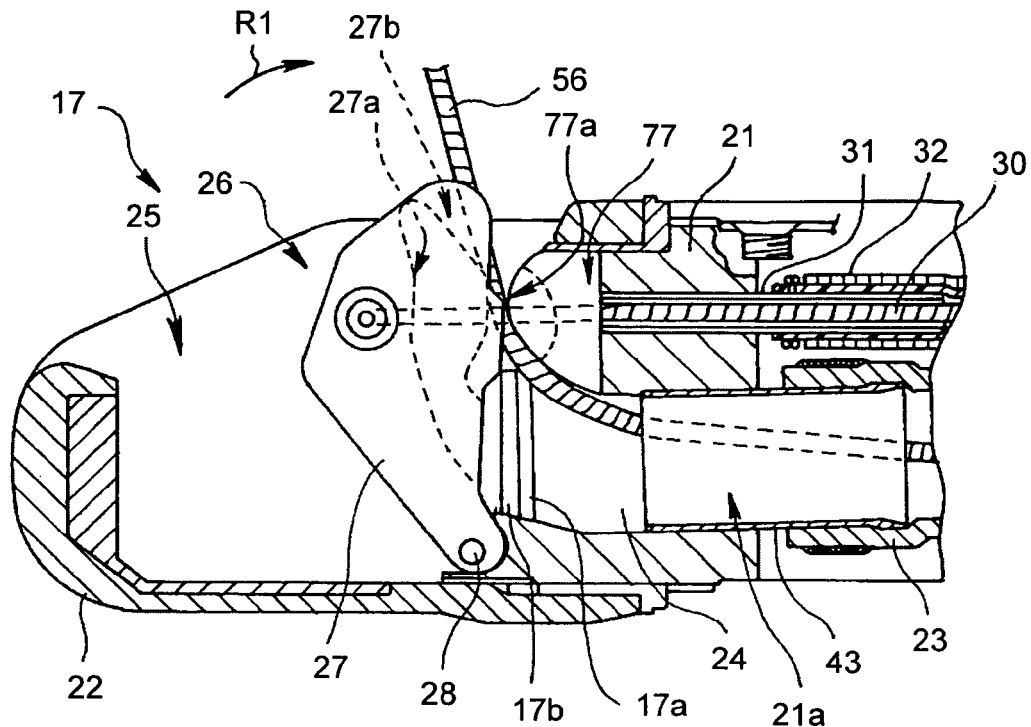
FIG. 18 is a diagram of the distal end portion of the endoscope in which the treatment instrument raiser is rotated by a predetermined amount from the state shown in FIGS. 16 and 17 to raise the guide wire, and a portion of a guiding surface of the treatment instrument raiser is brought into contact with the second stopper portion which regulates the rotation.
Figure 19:
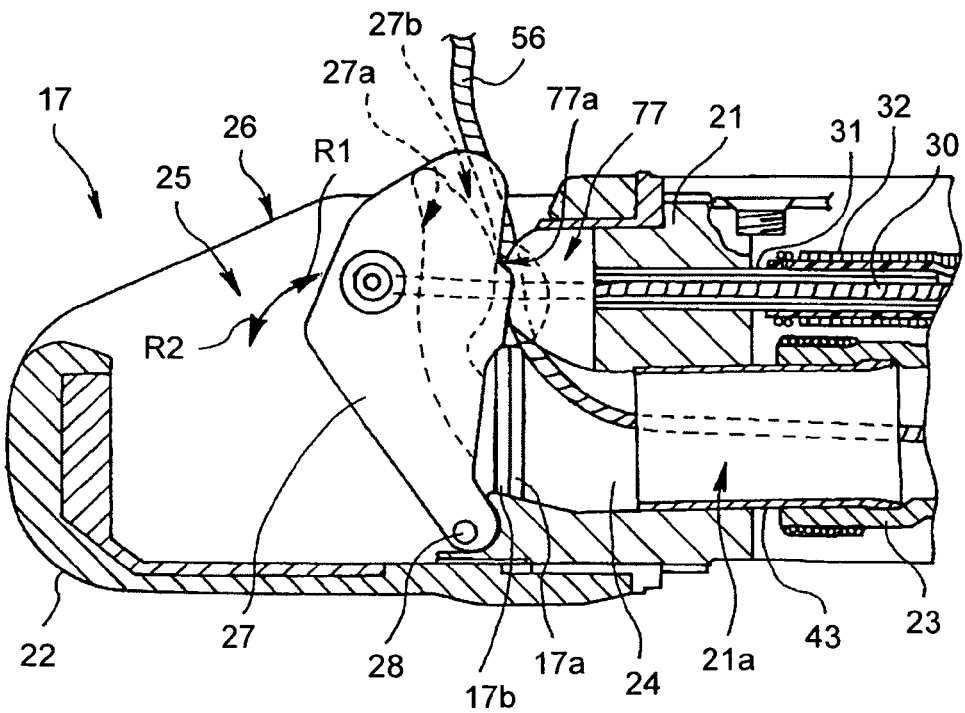
FIG. 19 is a diagram of the distal end portion of the endoscope in which the treatment instrument raiser is further rotated by a predetermined amount from a state of FIG. 18 to arrange the treatment instrument raiser at a maximum rising position thereby securing the guide wire with a slit.

FIGS. 16 to 19 are enlarged perspective views of a relevant portion of the distal end portion of the endoscope of FIG. 1. Among the drawings, FIG. 16 is a sectional view along line III-III of FIG. 2. FIG. 17 is a top view of the distal end portion of the endoscope in an initial state of FIG. 16. Here, FIGS. 16 and 17 show the distal end portion in a state where the treatment instrument raiser 27 has not been raised and the guide wire 56 sticks out from the channel opening. The state shown in FIGS. 16 and 17 will be referred to as an initial state. FIG. 18 is a diagram of the distal end portion of the endoscope in which the treatment instrument raiser 27 is rotated by a predetermined amount from the state shown in FIGS. 16 and 17 to raise the guide wire 56, and a portion of the guiding surface 27*a* of the treatment instrument raiser 27 is brought into contact with the second stopper portion 17*b* which regulates the rotation of the treatment instrument raiser 27. FIG. 19 is a diagram of the distal end portion of the endoscope in which the treatment instrument raiser 27 is further rotated by a predetermined amount from the state of FIG. 18 and arranged at the maximum rising position, thereby securing the guide wire 56 with the slit 27*b*.

After the guide wire 56 is inserted into the treatment instrument insertion port 40 of the operation portion 13 from the opening 40*a* (see FIG. 1) from a back end located close to the operator of the treatment instrument (not shown) such as a catheter inserted inside the treatment instrument insertion channel 23, the distal end of the guide wire 56 is guided toward the channel opening 26 as shown in FIG. 16 and the distal end of the treatment instrument is arranged inside the treatment instrument insertion channel 23. Here, a portion of the guide wire 56 is placed on the treatment instrument guiding surface 27*a* of the treatment instrument raiser 27.

While keeping the state as described above, the operator operates the operation knob 48 (see FIG. 1). In other words, the operator performs the rotation operation of the operation knob 48 in a predetermined direction so as to raise the treatment instrument raiser 27. Then, the rotating force of the operation knob 48 is converted into a force to pull the raising wire 30 via the predetermined holder engaging/driving mechanism (not shown). When the raising wire 30 is pulled, the treatment instrument raiser 27 starts to rotate around the holder rotation support point 28 in the direction of arrow R1 (clockwise direction in FIG. 16) as shown in FIG. 16.

Once the treatment instrument raiser 27 starts to rotate in the above mentioned direction, the guide wire 56 which is placed on the treatment instrument guiding surface 27*a* of the treatment instrument raiser 27 starts to be raised toward a side of the channel opening 26.

If the guide wire 56 is in the position shown by a solid line in FIG. 17, in other words, if the guide wire 56 is inside the slit 27*b* of the treatment instrument guiding surface 27*a*, the guide wire 56 remains at the position (predetermined intended position at which the guide wire 56 is to be placed) while being raised.

On the other hand, if the guide wire 56 is in a position (position at which the guide wire 56 is not intended to be placed) shown by a dotted line in FIG. 17, for example, in other words, if the guide wire 56 is not inside the slit 27*b* of the treatment instrument guiding surface 27*a* and bent toward a side of the side wall 25*a* of the housing chamber 25 and the treatment instrument raiser 27, the guide wire 56 is raised as follows.

The guide wire 56 is raised along with the rotation of the treatment instrument raiser 27 toward the rising direction, and moves toward a side of the side wall 25*a* of the housing chamber 25 on the treatment instrument guiding surface 27*a* of the treatment instrument raiser 27 as if slipping off from the treatment instrument guiding surface 27*a*. Here, the guide wire 56 slides over the guide wire guiding portion 27*c* in a direction toward the slit 27*b* of the treatment instrument raiser 27. The slipping movement of the guide wire 56, however, is stopped when the guide wire 56 is brought into contact with an edge portion 27*cc* of the guide wire guiding portion 27*c* of the treatment instrument raiser 27. In other words, when the guide wire 56 comes to be held by the edge portion 27*cc* of the guide wire guiding portion 27*c*, the guide wire 56 does not slip farther toward the side of the side wall 25*a* of the housing chamber 25, and is raised.

While the above state is maintained (while the guide wire is held by the edge portion 27*cc*), the treatment instrument raiser 27 raises the guide wire 56 to a certain degree. The guide wire 56 has an elastic tension to return in a direction to recover a linear state. Hence, when the guide wire 56 is raised to a certain degree, a force is applied to the guide wire 56 in a direction of arrow D shown in FIG. 17. Then, the guide wire 56 moves over the treatment instrument guiding surface 27*a* toward the slit 27*b* of the treatment instrument guiding surface 27*a* from the edge portion 27*cc* of the guide wire guiding portion 27*c* while being raised by the treatment instrument raiser 27. When the treatment instrument raiser 27 rotates up to the position shown in FIG. 18, the guide wire 56 inevitably falls inside the slit 27*b*.

An outer periphery of the treatment instrument guiding surface 27*a* is formed in a smooth shape leading to the slit 27*b*. In particular, a region extending from the guide wire guiding portion 27*c* to the slit 27*b* on the outer periphery is smoothly inclined starting from the guide wire guiding portion 27*c* as a top and through the edge portion 27*cc* to the slit 27*b*. The guide wire 56 which moves from the edge portion 27*cc* to the slit 27*b* side smoothly moves inside the slit 27*b* without being obstructed by the presence of the outer periphery. Thus, the guide wire guiding portion 27*c* can move the guide wire 56 to the edge portion 27*cc* side along with the raising operation of the treatment instrument raiser 27, and thereafter the guide wire guiding portion 27*c* can surely guide the guide wire 56 inside the slit 27*b* so that the guide wire 56 is brought into the state shown in FIG. 18.

On the other hand, when the guide wire 56 is not inside the slit 27*b* of the treatment instrument guiding surface 27*a* and bent toward a side opposite to the side of the side wall 25*a* of the housing chamber 25 and the treatment instrument raiser 27, i.e., to an outward direction of the distal end portion 17 of the endoscope 1, the guide wire 56 moves toward the slit 27*b* on the treatment instrument guiding surface 27*a* of the treatment instrument raiser 27 along with the raising operation. Then, the guide wire 56 inevitably comes inside the slit 27*b* while being raised by the treatment instrument raiser 27 to take the position shown in FIG. 18 similarly to the case described above.

Even when the guide wire 56 is off from the slit 27*b*, the treatment instrument raiser 27 having the above described structure can surely place the guide wire 56 inside the slit 27*b* before its rotating movement is stopped by the second stopper portion 17*b* by raising the guide wire 56 in the direction of arrow R1 (see FIG. 16) and adjusting the arranged state of the guide wire 56. Therefore, the treatment instrument raiser 27 can raise the guide wire 56 placed inside the slit 27*b* up to the state shown in FIG. 18 (state facing toward the channel opening 26) without making the guide wire 56 erroneously sandwiched at an unintended position (pseudo-fixed state), for example, a position between the treatment instrument raiser 27 and the side wall 25*a* of the housing chamber 25. In the state shown in FIG. 18, a portion of the treatment instrument guiding surface 27a of the treatment instrument raiser 27 is brought into contact with the second stopper portion 17b, and the rotation of the treatment instrument raiser 27 is stopped.

When the guide wire 56 in the state shown in FIG. 18 is moved in the axial direction of the endoscope 1, the guide wire 56 guided to the channel opening 26 can be inserted into a desirable duct such as the pancreatic duct, bile duct, hepatic duct, or the like. If a predetermined treatment instrument has already been inserted with the use of the guide wire 56 as a guide, such a treatment instrument can be withdrawn.

In the present embodiment, the treatment instrument raiser 27 can be rotated further from the state shown in FIG. 18. Prior to the further rotation of the treatment instrument raiser 27 from the state shown in FIG. 18 in the direction of arrow R1, the restriction on the rotation of the treatment instrument raiser 27 by the second stopper portion 17b is removed. For this purpose, the traction knob 64 (see FIG. 9) of the operation portion 13 is rotated so that the traction wire 69 is pulled in the direction of traction. Then the second stopper potion 17b comes to be housed in the side wall 25a of the housing chamber 25 and takes the position shown in FIG. 8. The range of rotation of the treatment instrument raiser 27 is delimited by a position where the treatment instrument raiser 27 comes into contact with the first stopper portion 17a, i.e., the maximum rising position shown in FIG. 19. In this state, the guide wire 56 is sandwiched between the slit 27b of the treatment instrument raiser 27 and the guiding surface 77a of the insulating member 77 and also fits into the slit 27b. Thus, the movement of the guide wire 56 in the axial direction is restricted and the guide wire 56 is held at the position. While the guide wire 56 is held at the position, the insertion and the withdrawal of the treatment instrument into and from the pancreatic duct, bile duct, hepatic duct, or the like can be easily performed.

In order to release the guide wire 56 from the position where the guide wire 56 is held, the operator operates the operation knob 48 (see FIG. 1) and rotates the operation knob 48 in a direction opposite to the direction of rising of the treatment instrument raiser 27. Then, the rotating force of the operation knob 48 loosens the raising wire 30 via the predetermined holder engaging/driving mechanism (not shown). When the raising wire 30 is loosened, the treatment instrument raiser 27 starts to rotate around the holder rotation support point 28 in the direction of arrow R2 (anticlockwise direction in FIG. 19) as shown in FIG. 19. Eventually, the treatment instrument raiser 27 returns to the state of FIG. 16. Thus, the guide wire 56 is released from the held state. Therefore, the guide wire 56 can be withdrawn from the pancreatic duct, bile duct, hepatic duct, or the like.

As described above, according to the present embodiment, when the guide wire 56 is raised along with the raising operation of the treatment instrument raiser 27, the guide wire 56 is not erroneously sandwiched and held at an unintended position and the guide wire 56 can be surely guided to the slit 27b of the treatment instrument raiser 27, since the guide wire guiding portion 27c is formed in a portion of the treatment instrument guiding surface 27a of the treatment instrument raiser 27. Therefore, the pseudo-fixed state can be surely prevented, and an outer cladding of the guide wire 56 is not ripped, whereby the security can be guaranteed and simultaneously a secure fixed state can be obtained.

Further, since the rising range of the treatment instrument raiser 27 is set in a two-step manner, according to which two rising ranges are set, and when the treatment instrument raiser 27 moves in the normal rising range, the insertion and the withdrawal of the guide wire 56 are allowed, whereas when the treatment instrument raiser 27 moves in the rising range whose highest position is the maximum rising range, the guide wire 56 is maintained in a held state. Therefore, the treatment instrument raiser 27 can be stably raised while the buckling of the treatment instrument can be prevented. At the same time, the guide wire 56 can be surely brought into the fixed state.

Further, the rising angle between the upper limit position within the normal rising range and the maximum rising position is controlled not at the operation portion but at a portion near the distal end portion of the endoscope 1, i.e., near the treatment instrument raiser 27. Therefore, the rising angle does not change in accordance with the fluctuation in the raising wire 30, difference in the shape of insertion portion, temporal degradation and the like, whereby the rising angle can be stably controlled continuously.

In the endoscope of the present embodiment, two stopper portions are utilized as appropriate as the rising range regulating mechanism as shown in FIGS. 7 to 11, whereby the rising range of the treatment instrument raiser 27 is controlled in two stages, i.e., a so-called two-stage raising mechanism is realized. The mechanism that realizes the two-stage raising mechanism is not limited to the above mechanism and a following mechanism may be applied, for example.

Figure 20:
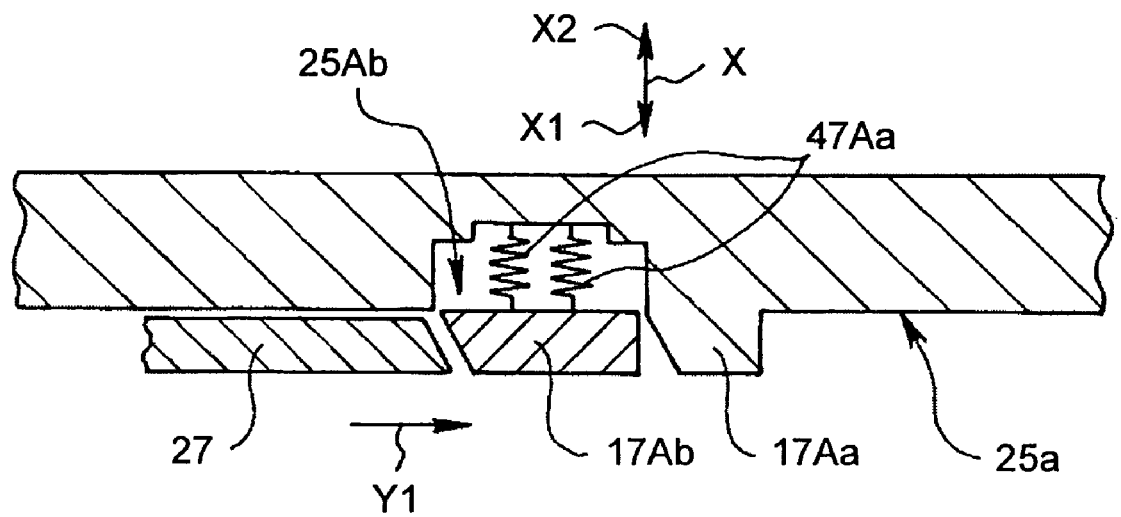
FIG. 20 is a diagram of another example of the rising range regulating mechanism in the endoscope of FIG. 1 in a normal state where the second stopper portion is projected.
Figure 21:
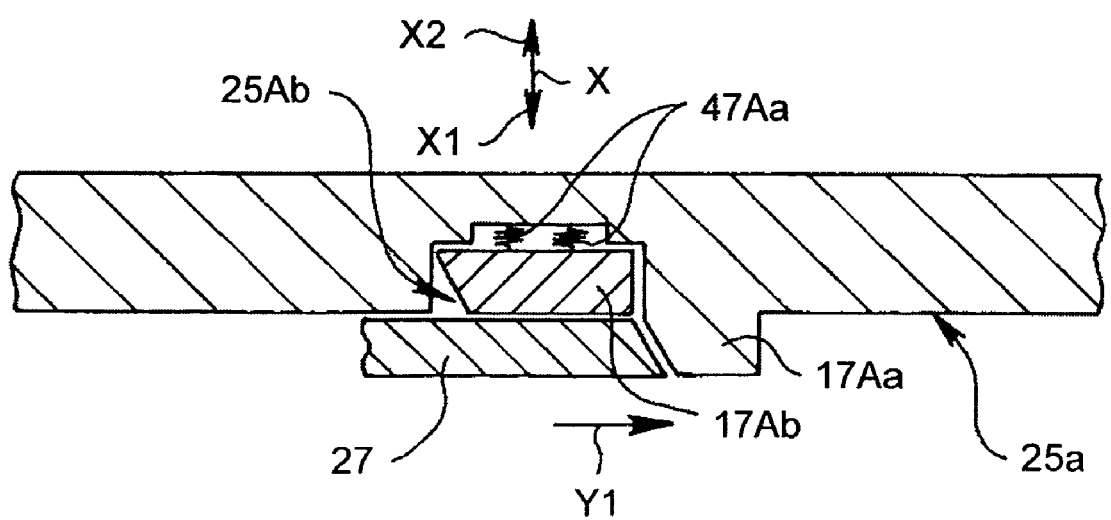
FIG. 21 is a diagram of the rising range regulating mechanism of FIG. 20 in a state where the second stopper portion is housed in an inner wall and a maximum rising position of the treatment instrument raiser is regulated by a first stopper portion.

FIGS. 20 and 21 show another example of the rising range regulating mechanism which realizes the two-stage raising mechanism of the treatment instrument raiser of the endoscope according to the present embodiment. FIG. 20 shows a second stopper portion 17Ab in a normal state, i.e., protruding state. FIG. 21 shows the second stopper portion 17Ab housed in the inner wall in a retracted state, where the maximum rising position of the treatment instrument raiser 27 is regulated by a first stopper portion 17Aa.

The second stopper portion 17Ab is configured so as to be able to protrude and retract taking the position in the side wall 25a (state shown in FIG. 21) or the position protruding toward inside the housing chamber 25 from the side wall 25a (state shown in FIG. 20).

A housing portion 25Ab is formed so as to house the second stopper portion 17Ab at a position in the side wall 25a. On a bottom surface of the housing portion 25Ab, a expandable elastic member 47Aa is arranged. The second stopper portion 17Ab is supported by the elastic member 47Aa. While the second stopper portion 17Ab is in a normal state, the second stopper potion 17Ab is constantly biases in a direction of arrow X1 shown in FIGS. 20 and 21, i.e., in a direction of protrusion, by the elastic member 47Aa. The above state (state of FIG. 20) is the normal state in the present example.

A forward end portion of the second stopper portion 17Ab is an end surface at a side where a part of the treatment instrument raiser 27 is brought into contact with. This end surface is formed as an inclined surface having a predetermined angle corresponding to the contact surface of the treatment instrument raiser 27. Thus, when the part of the treatment instrument raiser 27 comes into contact with the second stopper portion 17Ab, the rising of the treatment instrument raiser 27 is stopped at this position temporarily.

In the state as described above, the raising operation of the treatment instrument raiser 27 is further performed, so that a part of the treatment instrument raiser 27 is pressed against the second stopper portion 17Ab and force of an amount equal to or larger than a predetermined amount is exerted on the second stopper portion 17Ab. Then, the second stopper portion 17Ab moves in the direction of arrow X2 shown in FIGS. 20 and 21 against the force exerted by the elastic member 47Aa. Thus, the second stopper portion 17Ab comes to be housed inside the housing portion 25Ab. Then, the treatment instrument raiser 27 is released from the restriction by the second stopper portion 17Ab, and becomes able to rise up to the maximum rising position at which the treatment instrument raiser 27 is restrained by the first stopper portion 17Aa. The above state (state of FIG. 21) is a state regulating the maximum rising position of the present example. When the treatment instrument raiser 27 stops the rising operation in the above state and leaves the position where the treatment instrument raiser 27 presses the second stopper portion 17Ab, the second stopper portion 17Ab returns to the protruding state (normal state) as shown in FIG. 20 due to the pressing force of the elastic member 47Aa.

With the above structure, the two-stage raising mechanism of the treatment instrument raiser 27 can be realized via the control of the protrusion and depression of the second stopper portion 17Ab with a more simple mechanism.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope, comprising:
    an insertion portion which has a distal end hard portion at a distal end side and a treatment instrument insertion channel inside, and is insertable into a body cavity;
    an operation portion which is connected to a proximal end side of the insertion portion; and
    a treatment instrument raiser which is arranged near a distal end side opening of the treatment instrument insertion channel in the insertion portion, has a treatment instrument guiding surface for guiding a treatment instrument, and able to rise according to an operation from the operation portion, wherein
    the treatment instrument raiser includes
    a slit which is formed on a distal end portion of the treatment instrument guiding surface and with which a guide wire guided toward the distal end side opening of the treatment instrument insertion channel can be engaged, the guide wire being configured for guiding a treatment instrument inserted into the treatment instrument insertion channel, and
    a guide wire guiding unit which is formed on an outer periphery, other than on the distal end portion where the slit is formed, of the treatment instrument guiding surface and serves to guide the guide wire into the slit, the outer periphery being a portion where a side surface of the treatment instrument raiser is intersected with the treatment instrument guiding surface, the guide wire guiding unit including a protrusion formed on a portion of the outer periphery of the treatment instrument guiding surface and upwardly extending therefrom, the protrusion being configured to prevent slippage of the guide wire from the treatment instrument guiding surface, and wherein
    the guide wire is configured to be guided into the slit by the guide wire guiding unit, when the treatment instrument raiser is raised by the operation from the operation portion.

2. The endoscope according to claim 1, wherein
the outer periphery of the treatment instrument guiding surface extending from the protrusion to the slit forms a smooth inclination starting from the protrusion as a top.

3. The endoscope according to claim 1, wherein
the distal end hard portion has a retraction portion to avoid an interference of the guide wire guiding unit at a time the treatment instrument raiser is raised by the operation from the operation portion.

4. The endoscope according to claim 1, further comprising
a rising range regulating mechanism which regulates a rising range of the treatment instrument raiser at at least two portions.

5. The endoscope according to claim 4, wherein
the rising range regulating mechanism includes
    a first stopper portion which regulates a maximum rising position of the treatment instrument raiser,
    a second stopper portion which can regulate a rise of the treatment instrument raiser at a predetermined rising position within a range extending from a rising starting position to the maximum rising position of the treatment instrument raiser, and
    a stopper driving mechanism which sets the second stopper portion at one of a position to regulate the rising position of the treatment instrument raiser and a position not to regulate the rising position of the treatment instrument raiser.

* * * * *